(12) United States Patent  (10) Patent No.: US 8,096,979 B2
Lina et al.  (45) Date of Patent: Jan. 17, 2012

(54) REDUCED PRESSURE TREATMENT SYSTEM HAVING A DUAL POROSITY PAD

(75) Inventors: Cesar Z. Lina, Universal City, TX (US); Keith Heaton, Poole (GB); Royce Johnson, Universal City, TX (US)

(73) Assignee: KCI Licensing, Inc., San Antonio, TX (US)

(*) Notice: Subject to any disclaimer, the term of this patent is extended or adjusted under 35 U.S.C. 154(b) by 299 days.

(21) Appl. No.: 12/491,419

(22) Filed: Jun. 25, 2009

(65) Prior Publication Data

US 2010/0022972 A1    Jan. 28, 2010

Related U.S. Application Data

(60) Division of application No. 11/803,117, filed on May 11, 2007, now Pat. No. 7,758,554, which is a continuation of application No. 10/600,061, filed on Jun. 20, 2003, now Pat. No. 7,722,582, which is a continuation of application No. 09/545,339, filed on Apr. 7, 2000, now Pat. No. 6,695,823.

(60) Provisional application No. 60/128,567, filed on Apr. 9, 1999.

(51) Int. Cl.
*A61F 13/00* (2006.01)
*A61F 15/00* (2006.01)
*A61M 1/00* (2006.01)

(52) U.S. Cl. ......................... 604/313; 602/46
(58) Field of Classification Search .................. 604/304, 604/305, 307, 313, 369; 602/41, 46
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |

(Continued)

FOREIGN PATENT DOCUMENTS

AU    550575 A1    8/1982

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Melanie Hand

(57) ABSTRACT

A wound closure system and method having a porous pad for providing a reduced pressure to a tissue site is disclosed. The porous pad comprises a porous material formed by spraying a chemical substance that cures to form the porous material which has a body and an outer surface. Both the body and the outer surface have pores wherein the average size of the pores in the outer surface is smaller than the average size of the pores in the body. The porous pad further comprises a pathway formed within the porous material that is adapted to fluidly communicate with a source of reduced pressure.

11 Claims, 11 Drawing Sheets

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,572,330 A | 3/1971 | Gander |
| 3,648,692 A | 3/1972 | Wheeler |
| 3,682,180 A | 8/1972 | McFarlane |
| 3,826,254 A | 7/1974 | Mellor |
| 3,978,855 A * | 9/1976 | McRae et al. .................... 602/46 |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A * | 11/1985 | Plaas et al. .................... 604/290 |
| 4,569,348 A | 2/1986 | Hasslinger |
| 4,605,399 A | 8/1986 | Weston et al. |
| 4,608,041 A | 8/1986 | Nielson |
| 4,636,643 A | 1/1987 | Nakamura et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,747,166 A | 5/1988 | Kuntz |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,948,575 A | 8/1990 | Cole et al. |
| 4,953,565 A | 9/1990 | Tachibana et al. |
| 4,969,880 A | 11/1990 | Zamierowski |
| 4,985,019 A | 1/1991 | Michelson |
| 4,997,425 A | 3/1991 | Shioya et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,147,338 A | 9/1992 | Lang et al. |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,419,913 A | 5/1995 | Podell et al. |
| 5,437,622 A | 8/1995 | Carion |
| 5,437,651 A | 8/1995 | Todd et al. |
| 5,466,229 A | 11/1995 | Elson et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,827,246 A | 10/1998 | Bowen |
| 5,885,254 A | 3/1999 | Matyas |
| 5,911,222 A | 6/1999 | Lawrence et al. |
| 6,071,267 A | 6/2000 | Zamierowski |
| 6,135,116 A | 10/2000 | Vogel et al. |
| 6,142,982 A | 11/2000 | Hunt et al. |
| 6,241,747 B1 | 6/2001 | Ruff |
| 6,252,129 B1 * | 6/2001 | Coffee ........................ 602/42 |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DM | 032185 | 2/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 9623743.3 | 11/1996 |
| GB | 2 333 965 A | 8/1999 |
| GB | 2 329 127 B | 8/2000 |
| JP | 4129536 | 4/1992 |
| JP | A 07-016256 | 1/1995 |
| JP | T 10-504484 | 5/1998 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 95/05204 | 2/1995 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax,"*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Response filed Mar. 8, 2010 to Final Action dated Jan. 26, 2010 in U.S. Appl. No. 11/803,117.

Examiner Interview Summary date mailed Mar. 12, 2010 in U.S. Appl. No. 11/803,117.

Examiner Interview Summary and Notice of Allowance date mailed Mar. 25, 2010 in U.S. Appl. No. 11/803,117.

Examiner Interview Summary date mailed Oct. 23, 2009 in U.S. Appl. No. 10/600,061.

Response filed Dec. 1, 2009 to Final Action dated Sep. 1, 2009 in U.S. Appl. No. 10/600,061.

Notice of Allowance/Allowability date mailed Jan. 11, 2010 in U.S. Appl. No. 10/600,061.

Amendment filed Nov. 18, 2009 to Final Action dated Sep. 2, 2009 in U.S. Appl. No. 11/803,117.

Final Office Action date mailed Jan. 26, 2010 in U.S. Appl. No. 11/803,117.

Jill Fowler, Jeanette Mchone, "Wound with Massive So Tissue Lost", North Carolina Baptist Hospital, Winston Salem, NC.

Huge Cost Savings and Improved Patient Care Predicted; Two-Ten Communications, Communciations House, 210 Olst Street, London EC1V 9UN.

International Search Report and Written Opinion date mailed Aug. 14, 2000; International Application No. PCT/US00/09258.

Japanese Official Action date mailed Sep. 2, 2008; Japanese Patent Application No. 2000-610537.

Non-Final Office Action date mailed Apr. 28, 2005 for U.S. Appl. No. 10/600,061.

Response filed Aug. 29, 2005 to Non-Final Office Action date mailed Apr. 28, 2005 for U.S. Appl. No. 10/600,061.

Non-Final Office Action date mailed Nov. 1, 2005 for U.S. Appl. No. 10/600,061.

Response filed May 1, 2006 to Non-Final Office Action date mailed Nov. 1, 2005 for U.S. Appl. No. 10/600,061.

Final Office Action date mailed Jul. 13, 2006 for U.S. Appl. No. 10/600,061.

Response filed Oct. 5, 2006 to Final Office Action date mailed Jul. 13, 2006 for U.S. Appl. No. 10/600,061.

Interview Summary dated Oct. 16, 2006 for U.S. Appl. No. 10/600,061.
Non-Final Office Action dated Dec. 6, 2006 for U.S. Appl. No. 10/600,061.
Response filed Mar. 6, 2007 to Non-Final Office Action dated Dec. 6, 2006 for U.S. Appl. No. 10/600,061.
Non-Final Office Action date mailed Oct. 17, 2007 for U.S. Appl. No. 10/600,061.
Response filed Jan. 17, 2008 to Non-Final Office Action date mailed Oct. 17, 2007 for U.S. Appl. No. 10/600,061.
Final Office Action date mailed Jun. 20, 2008 for U.S. Appl. No. 10/600,061.
Response filed Jul. 28, 2008 to Final Office Action date mailed Jun. 20, 2008 for U.S. Appl. No. 10/600,061.
Advisory Action date mailed Aug. 11, 2008 for U.S. Appl. No. 10/600,061.
RCE filed Sep. 25, 2008 for U.S. Appl. No. 10/600,061.
Non-Final office Action date mailed Dec. 12, 2008 for U.S. Appl. No. 10/600,061.
Response filed Mar. 12, 2009 to Non-Final office Action date mailed Dec. 12, 2008 for U.S. Appl. No. 10/600,061.
Supplemental Response filed Mar. 24, 2009 to Non-Final Office Action date mailed Dec. 12, 2008 for U.S. Appl. No. 10/600,061.
Communication concerning response date mailed Jun. 2, 2009 for U.S. Appl. No. 10/600,061.
Communication date mailed Jun. 23, 2009 vacating previous communication date mailed Jun. 2, 2009 for U.S. Appl. No. 10/600,061.
Final Office Action date mailed Sep. 1, 2009 for U.S. Appl. No. 10/600,061.
Restriction Requirement date mailed Feb. 6, 2009 for U.S. Appl. No. 11/803,117.
Response filed Mar. 26, 2009 to Restriction Requirement date mailed Feb. 6, 2009 for U.S. Appl. No. 11/803,117.
Restriction Requirement date mailed Jun. 2, 2009 for U.S. Appl. No. 11/803,117.
Response filed Jun. 17, 2009 to Restriction Requirement date mailed Jun. 2, 2009 for U.S. Appl. No. 11/803,117.
Non-Final Office Action date mailed Sep. 2, 2009 for U.S. Appl. No. 11/803,117.

* cited by examiner

REDUCED PRESSURE TREATMENT SYSTEM HAVING A DUAL POROSITY PAD

CROSS-REFERENCE TO RELATED APPLICATIONS

This application is a divisional of U.S. patent application Ser. No. 11/803,117 filed May 11, 2007 now U.S. Pat. No. 7,758,554, which is a continuation of U.S. patent application Ser. No. 10/600,061 filed Jun. 20, 2003 now U.S. Pat. No. 7,722,582, which is a continuation of U.S. patent application Ser. No. 09/545,339 filed Apr. 7, 2000, now U.S. Pat. No. 6,695,823 issued Feb. 24, 2004, which claims the benefit of U.S. Provisional Application No. 60/128,567, filed Apr. 9, 1999, and any amendments thereof. All of the above-referenced applications are hereby incorporated by reference.

BACKGROUND OF THE INVENTION

1. Field of the Invention

The present invention relates to the healing of wounds and, more particularly, but not by way of limitation, to methods, articles, and systems for closing wounds that is compact, self-contained, and includes a disposable wound fluids canister and a porous pad, which is biocompatible with the wound tissue to facilitate the healing of wounds, but does not adhere to the healing tissue.

2. Description of Related Art

Wound closure involves epithelial and subcutaneous tissue adjacent to the wound migrating towards the center of the wound until it closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but are also less able to successfully fight bacterial infection and, thus are less able to close the wound naturally. Such wounds have presented difficulties to medical personnel for many years.

The most common technique for closing open wounds has been the use of sutures or staples. Although such mechanical closure techniques are widely practiced and often effective, they suffer a major disadvantage by providing tension on the skin tissue adjacent the wound. That is, the tensile force required to achieve closure using sutures or staples causes very high localized stresses at the suture or staple insertion point. Such stresses commonly result in the rupture of the tissue at those points, which can eventually cause dehiscence in wounds, providing additional tissue loss.

Moreover, some wounds harden and inflame to such a degree due to infection that closure by stapling or suturing is not feasible. Wounds not reparable by suturing or stapling generally require prolonged hospitalization with its attendant high cost, and major surgical procedures, such as grafts of surrounding tissues. Examples of wounds not readily treatable with staples or sutures include large, deep, open wounds; decubitus ulcers; ulcers resulting from chronic osteomyelitis; graft site wounds; and partial thickness burns that subsequently develop into full thickness burns. The use of skin grafts in these situations can result in the encapsulation of bacteria and other impurities.

One solution to the problem of non-healing wounds has been demonstrated by applying a continuous negative pressure to the wound over an area sufficient to promote migration of epithelial and subcutaneous tissue toward the wound. A porous pad or other manifolding device may be used to distribute reduced pressure to the wound. The porous pad typically contains cells or pores that are capable of distributing reduced pressure and channeling fluids that are drawn from the wound. One drawback, however, to current designs is that new tissue growth may easily penetrate the cells or pores and effectively attach the pad to the wound. Upon removal of the pad from the wound, any tissue in-growth that has occurred must be physically separated from the pad. Typically, the pad removal involves tearing of new tissue, which not only disrupts the healing process but also may cause discomfort to the patient.

SUMMARY

The problems presented by existing treatment systems are solved by the system, articles and methods of the present invention. In accordance with one embodiment of the present invention, a method for providing a reduced pressure to a tissue site is provided. The method comprises spraying a chemical substance that cures to form a porous material having a body and an outer surface. Both the body and the outer surface have pores wherein the average size of the pores in the outer surface is smaller than the average size of the pores in the body. A portion of the outer surface is substantially conformable to the shape of the tissue site. The method further comprises providing a pathway for the reduced pressure to the porous material.

In another embodiment, providing a pathway for the reduced pressure to the porous material comprises inserting one end of a tube within the porous material prior to the chemical substance being cured. The other end of the tube is adapted to fluidly communicate with a source of reduced pressure.

In yet another embodiment, providing a pathway for the reduced pressure to the porous material comprises positioning one end of a tube adjacent the tissue site while spraying the chemical substance. One end of the tube is contained within the porous material after the chemical substance cures, and the other end of the tube is adapted to fluidly communicate with a source of reduced pressure.

In yet another embodiment, a porous pad for providing a reduced pressure to a tissue site is provided. The porous pad comprises a porous material formed by spraying a chemical substance that cures to form the porous material having a body and an outer surface. Both the body and the outer surface have pores wherein the average size of the pores in the outer surface is smaller than the average size of the pores in the body. A portion of the outer surface is substantially conformable to the shape of the tissue site. The porous pad further comprises a pathway formed within the porous material that is adapted to fluidly communicate with a source of reduced pressure.

In yet another embodiment, the chemical substance comprises a pressurized liquid before being sprayed. The chemical substance expels gas from the pressurized liquid when sprayed so that the chemical substance expands and hardens to form the porous material.

In another embodiment, a tissue treatment system is provided. The system comprises a porous material formed by spraying a chemical substance that cures to form the porous material having a body and an outer surface. Both the body the outer surface have pores wherein the average size of the pores in the outer surface is smaller than the average size of the pores in the body. A portion of the outer surface is substantially conformable to the shape of the tissue site. The system further comprises a pathway formed within the porous material that is adapted to fluidly communicate with a source of reduced pressure whereby reduced pressure is provided to the tissue site. The system further comprises a conduit operable to deliver the reduced pressure with a first end of the conduit being connectable to the pathway and a second end of the conduit being connectable to the source of reduced pressure.

Other objects, features, and advantages of the present invention will become apparent with reference to the drawings and detailed description that follow.

DETAILED DESCRIPTION OF ILLUSTRATIVE EMBODIMENTS

Figure 1:
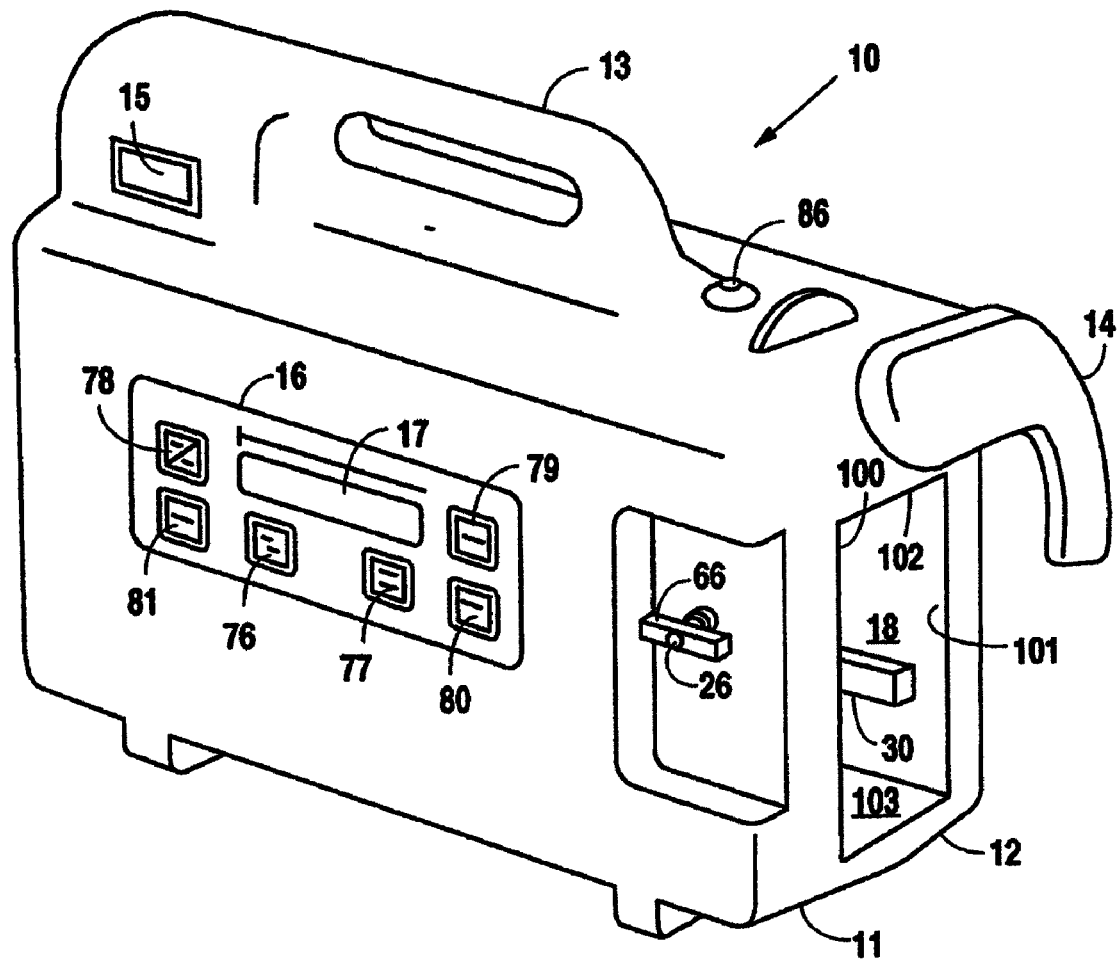
FIG. 1 is a perspective view depicting the vacuum pump unit of a wound closure apparatus constructed according to the teachings of the present invention.
Figure 2:
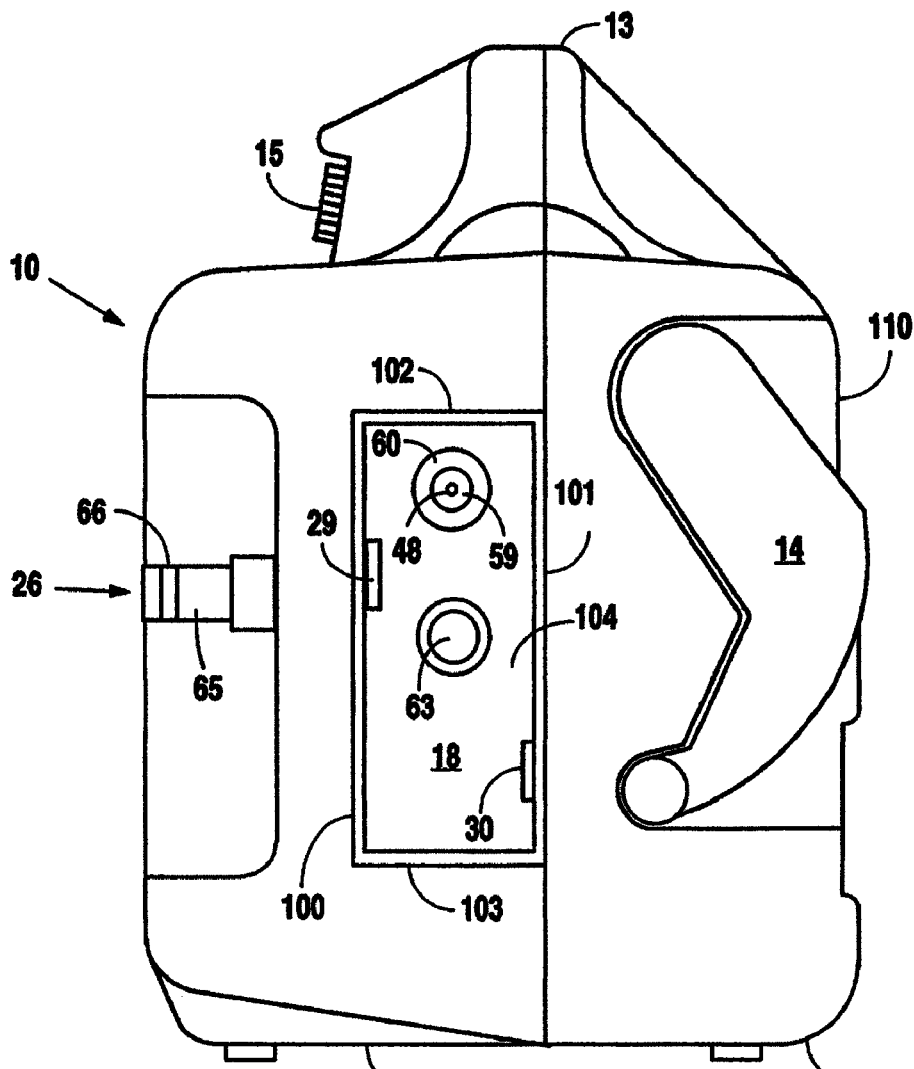
FIG. 2 is a right side plan view depicting the vacuum pump unit of FIG. 1.

As illustrated in FIGS. 1 and 2, front housing 11 and rear housing 12 connect together using any suitable means such as screws and fasteners to provide wound closure vacuum pump 10 with a small, compact, and easily portable carrying case. Consequently, front housing 11 and rear housing 12 connect together to form handle 13 that permits easy carrying of the wound closure apparatus 10. Except as may be otherwise evident from this description, the carrying case of the vacuum pump 10 is substantially as described and shown in WIPO Design No. DM/032185.

Figure 3:
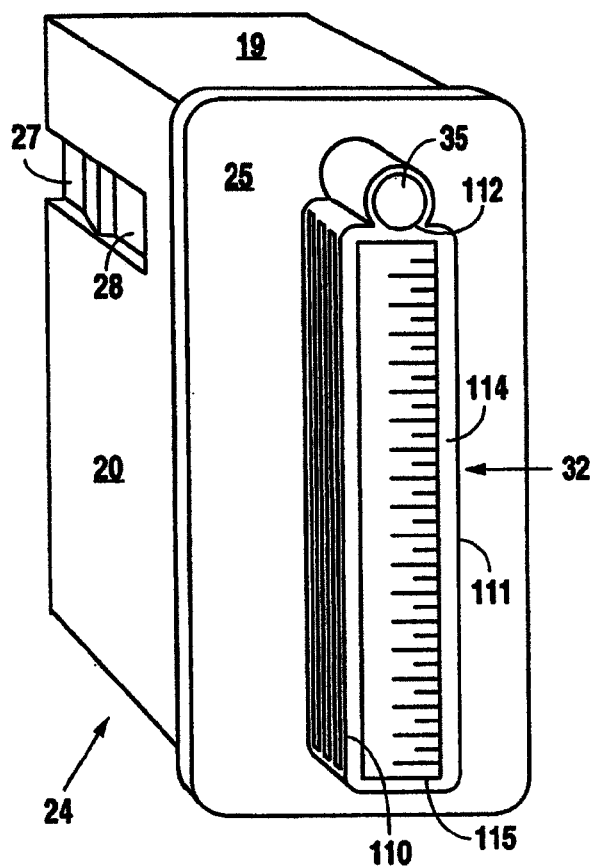
FIG. 3 is a perspective view depicting a wound drainage collection canister for use in conjunction with the vacuum pump unit of FIG. 1.
Figure 4:
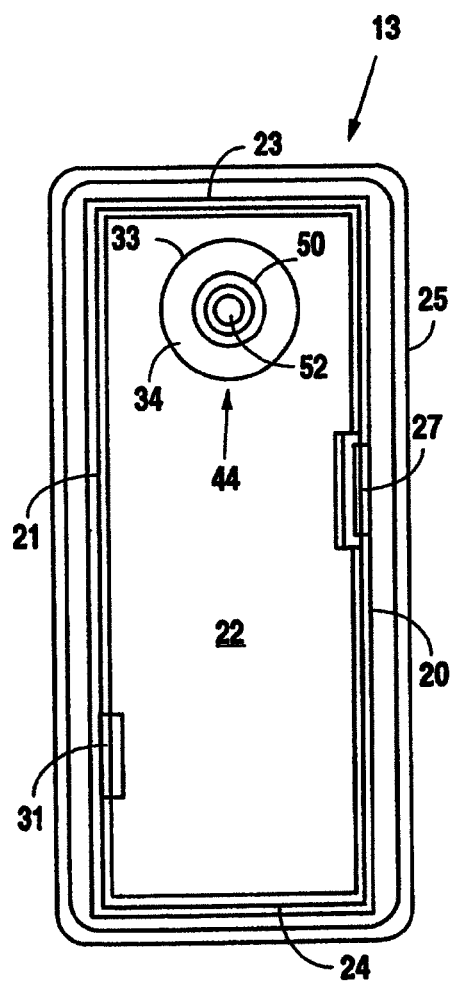
FIG. 4 is a rear plan view depicting the wound drainage collection canister of FIG. 3.
Figure 5:
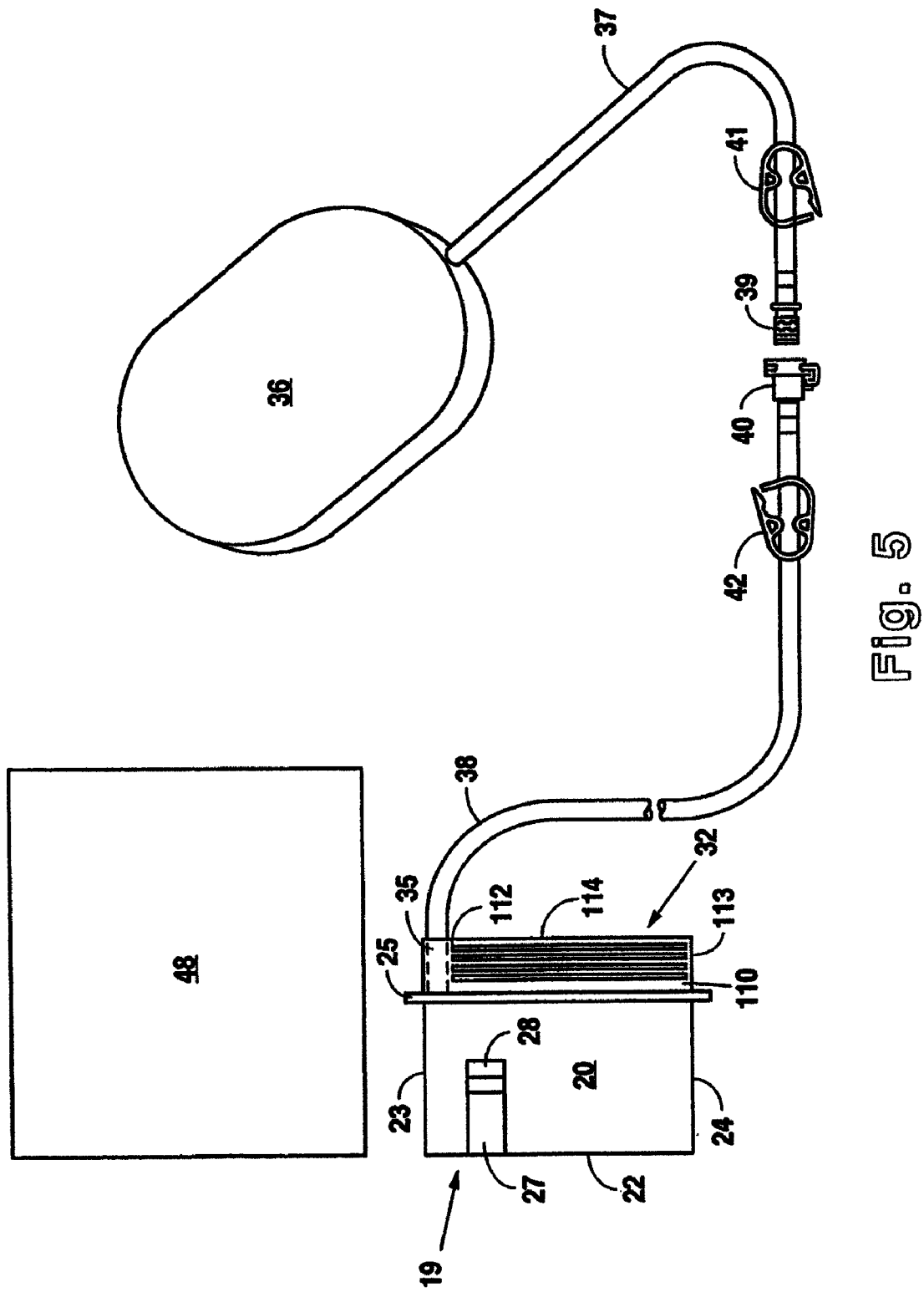
FIG. 5 is a perspective view depicting the connection of a wound drainage collection canister of FIG. 3 to a wound coverage pad.

Front housing 11 includes power switch 15 that is movable between an on and off position to permit user control of the delivery of power to the wound closure apparatus 10. Keypad 16 and liquid crystal display (LCD) 17 mount to front housing 11 to permit the programming of the wound closure apparatus 10. Chamber 18 is defined by integrally formed interior side walls 100 and 101, top wall 102, bottom wall 103 and rear wall 104. Side wall 100 is dependently attached to the interior of the front housing 11 by standard mounting hardware (not shown). The wound fluids collection canister 19, illustrated in FIGS. 3-5, is received within chamber 18. Side walls 100 and 101 each include a key 29 and 30, respectively, that aid in the alignment of wound fluids collection canister 19 within chamber 18. Furthermore, front housing 11 includes latch 26 to secure the wound fluids collection canister 19 within chamber 18.

Rear housing 12 includes arm 14 pivotally mounted to it within recess 110. An identical arm pivotally mounts to the opposite side of rear housing 12 within an identical recess. Arm 14 and its corresponding arm mounted on the opposite side of the rear housing 12 pivot from within their recesses to a position where they support the wound closure apparatus 10 at an angle. Arm 14 and its corresponding arm angularly support the wound closure apparatus 10 to permit easier user access to keypad 16. Arm 14 and its corresponding arm may also be used to permit hanging of apparatus 10 from a hospital bed foot board.

Canister 19 has a shape as shown in FIGS. 3 to 6. As illustrated in FIGS. 3 to 6, canister 19 includes side walls 20 and 21, top wall 23, bottom wall 24, back wall 22 and front wall 25 that define the rectangular chamber for receiving blood, pus, and other fluids emitted from a wound. Side walls 20 and 21 include key ways 27 and 31 respectively, that receive a respective one of keys 29 and 30 to provide easy alignment of canister 19 within chamber 18. Furthermore, key way 27 includes recess 28 that receives latch 26 to fasten canister 19 within chamber 18

Front wall 25 of canister 19 includes raised portion 32 extending therefrom to furnish a window that permits a user to determine the level of wound fluids within canister 19. Accordingly, raised portion 32 is transparent so that the level of wound fluids within canister 19 may be visually determined. Raised portion 32 includes side walls 110 and 111, top wall 112, bottom wall 113, and front face 114 that define a chamber which opens into the chamber defined by side walls 20 and 21, top wall 23, bottom wall 24, back wall 22 and front wall 25 of canister 19. Front face 114 of raised portion 32 includes graduations that demarcate the volume of wound fluid within canister 19. Additionally, side walls 110 and 111 of raised portion 32 include ridges that provide a gripping surface for the user during the insertion and removal of canister 19 from chamber 18.

Although raised portion 32 is transparent to permit the determination of the level of wound fluids within canister 19, side walls 20 and 21, back wall 22, top wall 23, bottom wall 24, and front wall 25 are opaque so that they are only translucent. As an alternative, the portions of canister 19 surrounding filter 46 may also be transparent. This enables a user to visually check for signs of contamination of filter 46. In this preferred embodiment, side walls 20 and 21, back wall 22, top wall 23, bottom wall 24, front wall 25, and raised portion 32 of canister 19 are fabricated from a plastic material.

Canister 19 includes inlet 35 that is formed integrally with top wall 112 of raised portion 32. Inlet 35 is cylindrical in shape and communicates with the interior of canister 19 to permit the transfer of wound fluids into canister 19. In this preferred embodiment, inlet 35 is also fabricated from a plastic material.

In order to prevent liquids sucked into the canister 19 from splashing directly onto cap 49, which mask the outlet 44, and to reduce foaming within the canister 19, inlet 35 has a blind inner end. Inlet 35 has a slot 35A so that drainage fluid is deflected downwardly into the raised handle portion 32 of the canister 19. Handle portion 32 may communicate with the main part of the canister 19 through one or more holes in wall 25. It is desirable to avoid foaming because this can give a false reading when a capacitance sensing device is used to sense when the canister 19 is filled. An anti-foaming material, e.g. a silicone, may be added to the canister 19, e.g. by coating the interior walls. It may also be advantageous to include a gel-forming substance, e.g. a polyacrylamide of modified starch in order to immobilize the drainage fluid. This is particularly useful if the apparatus is likely to be tilted.

Wound fluids (i.e. drainage) are communicated through inlet 35 into canister 19 via pad 36 and hoses 37 and 38. In this preferred embodiment, the portion of the pad 36 next to the vacuum tube 37 (i.e. inner portion or surface) is fabricated from an open cell polyurethane or polyether foam. The outer surface of the pad 36 in contact with the wound cavity 216 can consist of the same material as the inner portion or surface next to the vacuum tube 37 where the size of the pores is 100 microns of less. Hose 37 is inserted within pad 36 by making an incision in pad 36 and inserting the end of hose 37. Hose 37 can then be secured within pad 36 using any suitable means such as an adhesive or a flange. Preferably, the porous pad 36 has an elongated hole 300 (See FIG. 11) for the drainage tube 37 which is an interference fit with the tube 37. The hoses 37 and 38 are preferably made from medical grade PVC tube. Hose 38 mounts within inlet 35 using any suitable means such as adhesive or welding. Hoses 37 and 38 include luer lock connectors 39 and 40, respectively, (or the equivalent, such as any known quick disconnect type coupling) that attach together to permit communication between hoses 37 and 38. Furthermore, hoses 37 and 38 include pinch clamps 41 and 42, respectively, that are capable of sealing their respective hose 37 or 38 to prevent the flow of wound fluids. The porous pad 36 is preferably packaged in a sterile container together with its connector and clamp. When packaged, the clamps will be in their open condition.

The communication of wound fluids into canister 19 requires the securing of pad 36 over a wound. Pad 36 is secured over a wound using cover 43 which is fabricated from a plastic material and includes an adhesive on one side that sticks to human skin. Wound cover 43 is conveniently a surgical drape material comprising a sheet of elastomeric material coated peripherally or overall with a pressure-sensitive adhesive, such as an acrylic adhesive. The elastomeric or rubbery nature of the wound cover 43 is important because it accommodates changes in pressure in the wound area during intermittent operation of the vacuum pump 84. The wound cover 43 is preferably a polyurethane film with a removable backing sheet, i.e. of polythene to protect the adhesive surface.

A high degree of reticulation in the inner portion or surface of the porous pad 36 next to the vacuum tube 37 is desirable to achieve good permeability when the pad 36 is under suction. The outer surface of the pad 36 next to the wound, however, is smooth and contains pores of approximately 100 microns in diameter to allow for vacuum air flow through the pad 36 while preventing the healing tissue from cross linking with the pad 36. While the upper range of pore size is not exactly known, it is between 100 microns and 1000 microns (one millimeter). The lower end of the pore size is simply large enough to allow air and fluids to flow therethrough which could be as small as one micron.

There are several different ways to prepare a pad 36 for use with the wound drainage apparatus 10 which contains an outer surface with the preferred specifications. One way is to make a porous pad 36 out of a material which consists entirely of micropores (not shown) with a diameter of approximately 100 microns or less, or blow the pad 36 in such a way that the portion to be inserted into the wound cavity contains the micropores of a diameter of approximately 100 microns or less as will be subsequently described. A micropore is an opening in the pad 36 of approximately 100 microns or less.

Figure 11:
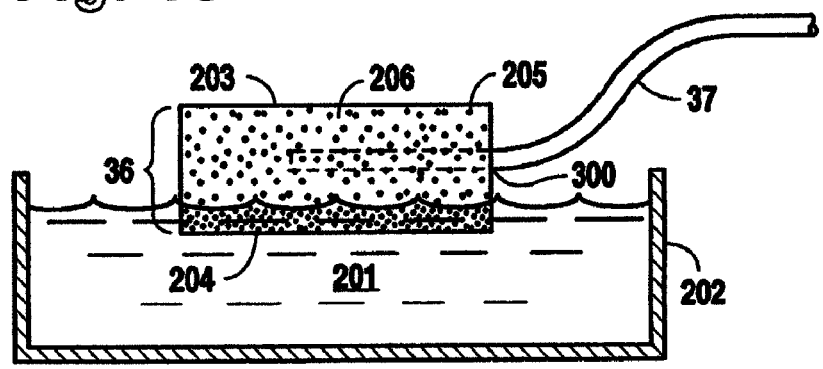
FIG. 11 is a porous wound pad being dipped into a solution.
Figure 12:
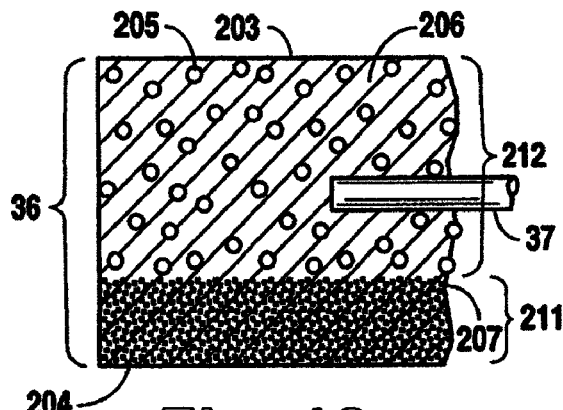
FIG. 12 is a porous wound pad with varying porosity on two sides (with tube).

Referring to FIGS. 11 and 12, a second way to create the pad 36 is to dip the portion of the pad 36 which is to be placed inside the wound in a liquid coating material 201 which dries into the pad 36 acting as a bulking agent thereby reducing the diameter of the pad pores 205 to approximately 100 microns or less. This effectively creates a smooth outer surface with a pore size of approximately 100 microns or less, hereinafter called micropores 207, to be placed in the wound cavity 216. An inner surface can have pores 205 of a size of greater than 100 microns which have a greater vacuum compatibility with the vacuum tube 37.

In FIG. 11, a porous wound pad being dipped into a solution 201 is shown. FIG. 11 shows a porous wound pad 36, with top 203, bottom 204, and side 206. The pores 205 of the porous wound pad 36 are a vacuum compatible size. A vacuum tube 37 is shown in the side 206 of the porous wound pad 36. The pad 36 is being dipped to approximately 1 millimeter into a liquid coating material 201, such as a liquid hydrophilic foam solution, held in a flat tray 202, which when hardened acts as a bulking agent to form a smooth micropore layer 211 with micropores 207 of a diameter of approximately 100 microns or less. This allows for the flow of negative air pressure and fluids through the pad 36 without compromising the healing tissue surface. The coating of the pad 36 can occur directly before insertion into the wound cavity 216, allowing enough time for drying, or the pad 36 can be coated during manufacturing. Furthermore, for certain types of wounds it may be necessary to mix an antimicrobial agent such as Neosporin with the liquid coating material 201 so as to create a modified pad surface which is difficult for bacteria to stick to thus preventing bacterial migration through the pad 36. The addition of the coating to the pad 36 does not hamper the ability to trim the pad 36 to conform to the wound cavity 216.

FIG. 12 shows a cross section of a porous wound pad 36 with varying porosity on one surface (with tube). This varying porosity can result from the porous pad 36, with top 203, bottom 204 and side 206, being dipped in the liquid coating material 201 as described in FIG. 11. This pad 36 contains an upper pore layer 212 with vacuum compatible pores 205 and a smooth micropore layer 211 with healing compatible pores 207 which have a diameter of approximately 100 microns or less. By having a size of approximately 100 microns or less, tissue cannot grow into the micropore layer 211. Again the liquid coating material 201 (a) can be modified with an antimicrobial agent such as Neosporin to deter bacterial migration through the pad 36, or (b) forms a tissue compatible lubricious surface that is growth factor impregnated or is a molecular graft.

Figure 13:
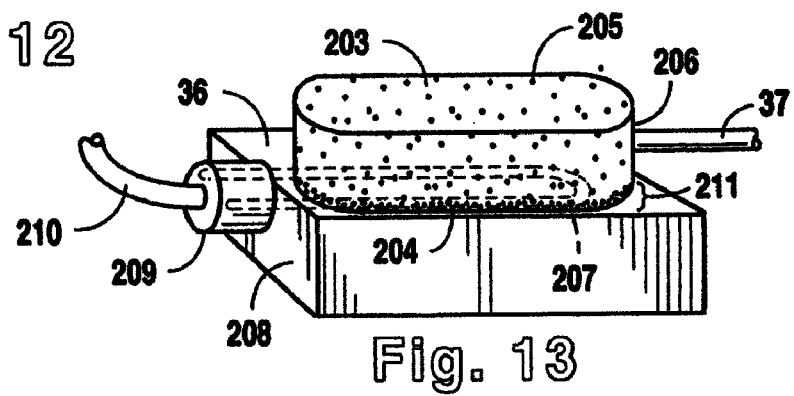
FIG. 13 is a side of a porous wound pad being melted by a heat source.

Referring to FIG. 13, another way of creating the optimum outer pad surface is to take a porous pad 36 with pores 205 that may have a diameter greater than 100 microns and heat that pad 36 on the side to be placed inside the wound cavity 216 with a heat source 208 so as to shrink or melt the pore size to a diameter of approximately 100 microns or less while maintaining a smooth texture. In FIG. 13, a side of a porous wound pad being melted by a heat source is shown. The pad 36, with top 203, bottom 204, and side 206 and containing pores 205 of vacuum compatible pore size, is shown on a hot plate 208. This hot plate 208 has a standard current adapter 209 and plug 210. While a hot plate 208 was used in this illustration, any heat source could be used. The heat source 208 was simply necessary to melt the surface of the pad 36 partially so as to create a smooth micropore layer 211 with healing compatible micropores 207 of approximately 100 microns or less.

Figure 17:
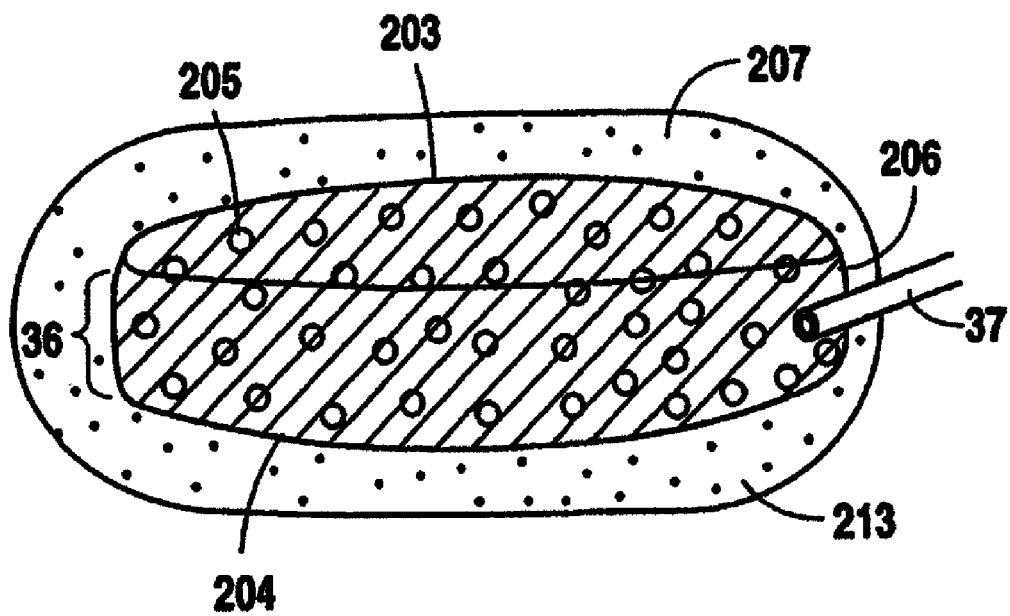
FIG. 17 is a porous sock wrapped around the porous wound pad (with tube).
Figure 18:
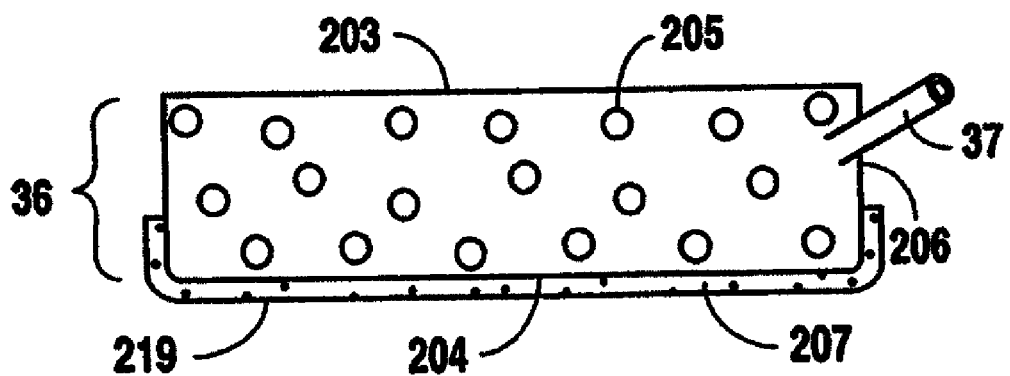
FIG. 18 is a porous wound pad with a removable micropore layer (with tube).

Referring to FIGS. 17 and 18, the porous pad 36 can be made with a smooth outer surface of approximately 100 microns or less by taking a pad 36 with vacuum compatible pores 205 and placing the pad 36 within a porous sock 213 which is smooth and contains pores 207 with a diameter of approximately 100 microns or less. The sock-covered pad 36 is then placed inside the wound cavity (not shown in this Figure). FIG. 17 shows a porous wound pad 36 situated within a porous sock 213. The pad 36, with top 203, bottom 204, and side 206, has vacuum compatible pores 205 and a vacuum tube 37 for use in extending the negative air pressure through the pad 36. The porous sock 213 contains healing compatible pores 207 of a diameter of approximately 100 microns or less and acts as a covering being placed over the porous wound pad 36 before insertion into the wound cavity 216. If any trimming of the pad 36 is needed it can be done before the pad 36 is placed in the sock 213 before insertion into the wound cavity 216.

Referring specifically to FIG. 18, a variation of the technique demonstrated in FIG. 17 would be to affix a smooth porous membrane 219 only to the face of the pad 36 that is to be placed into the wound cavity 216. This membrane 219 contains pores of a diameter of approximately 100 microns or less. The porous sock 213 or membrane 219 may be composed of TEFLON, rayon, or a similar material. Knit rayon film is often used for conventional dressings to try to accelerate the growth of granulation tissue. The membrane 219 may form a tissue compatible lubricious surface that is growth factor impregnated and antimicrobial. In FIG. 18, a porous wound pad 36 with a removable membrane 219 is shown. The pad 36, with top 203, bottom 204, and side 206 and vacuum compatible pores 205, contains a vacuum tube 37 for use in extending the negative air pressure through the pad 36 for aspiration of the wound cavity 216. The removable membrane material 219, such as Teflon or rayon, contains healing compatible micropores 207 of a diameter of 100 microns or less. This membrane material 219 can be placed around the portion of the pad 36 which is to go into the wound cavity 216. The membrane 219 can be held in place on the pad 36 by any biocompatible means such as an adhesive.

Figure 14A:
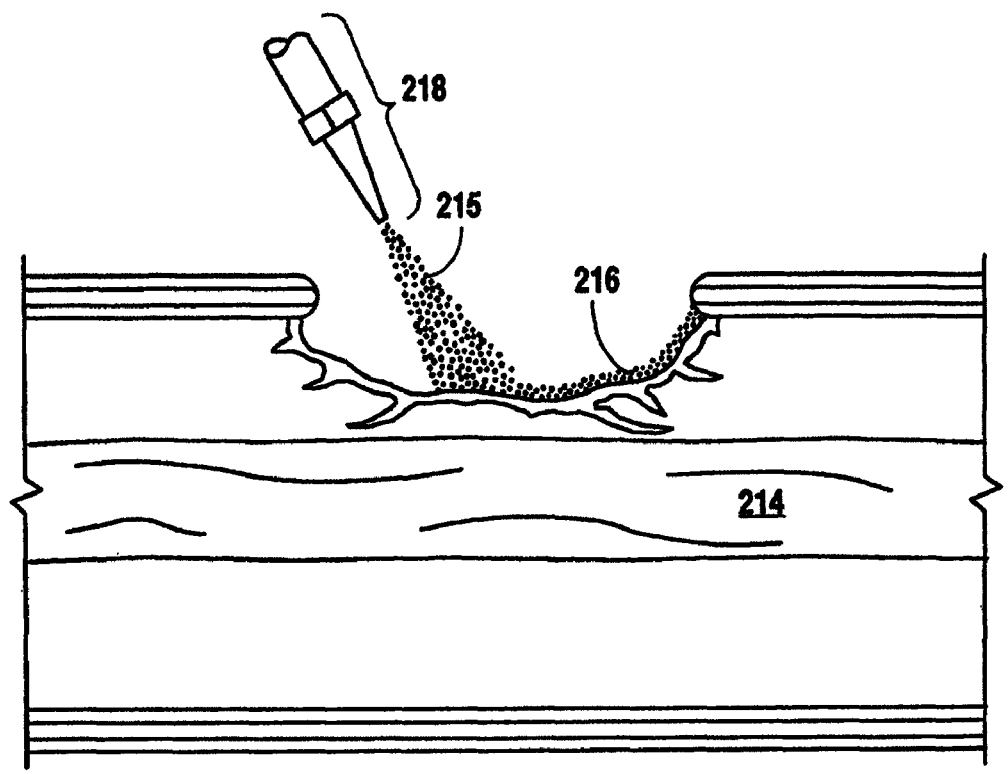
FIG. 14A is a cross section of chemical being sprayed into the wound.
Figure 14B:
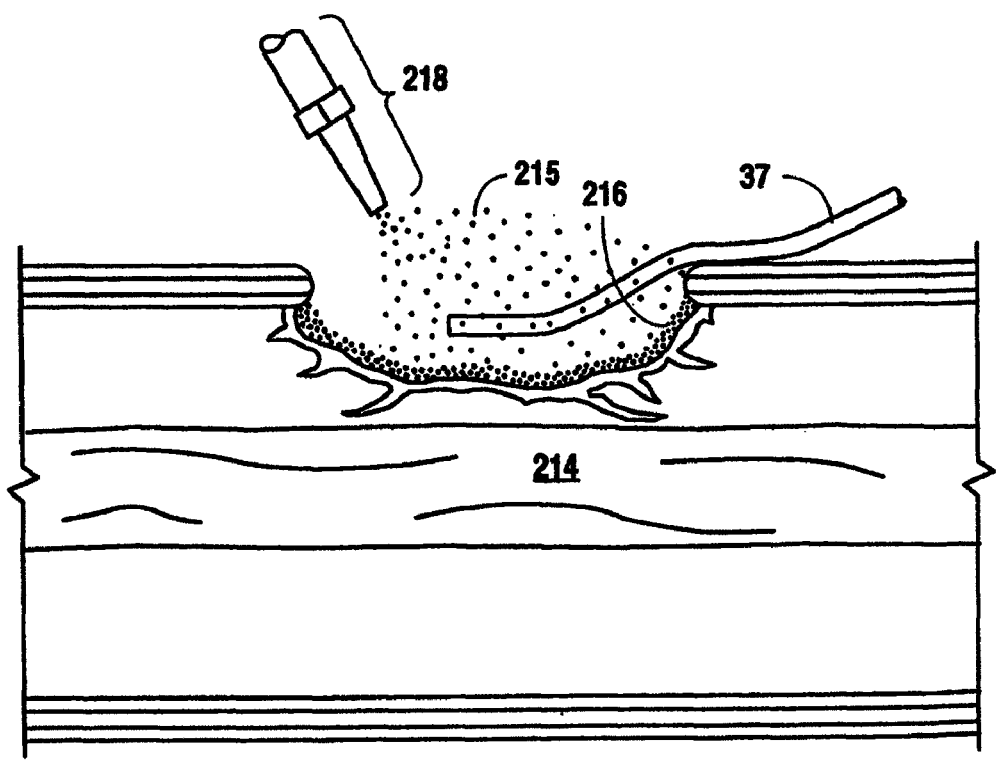
FIG. 14B is a cross section of chemical being sprayed into the wound (with tube).
Figure 15:
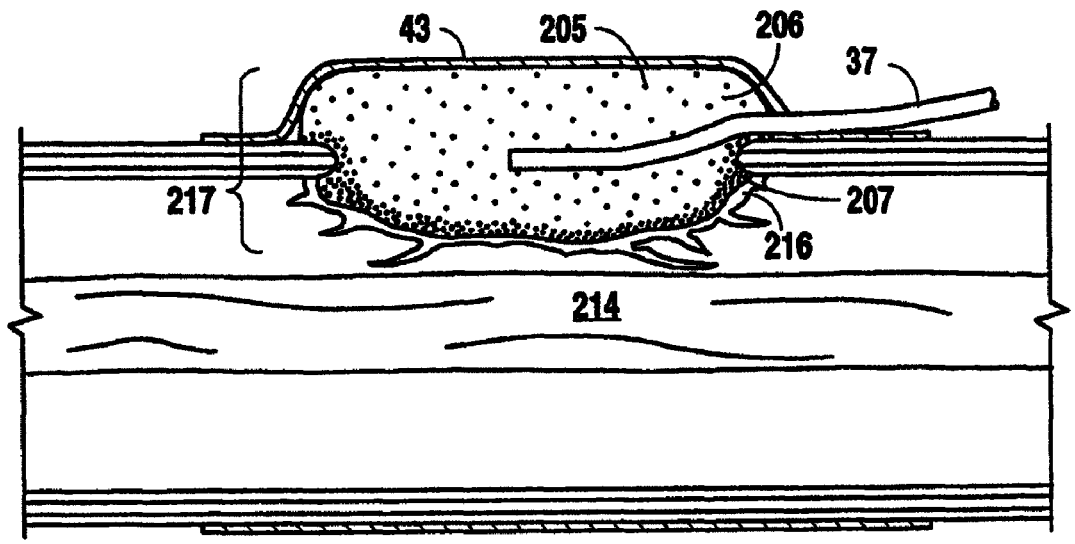
FIG. 15 is a cross section of a wound where spraying of the chemical has been completed (with tube).
Figure 16:
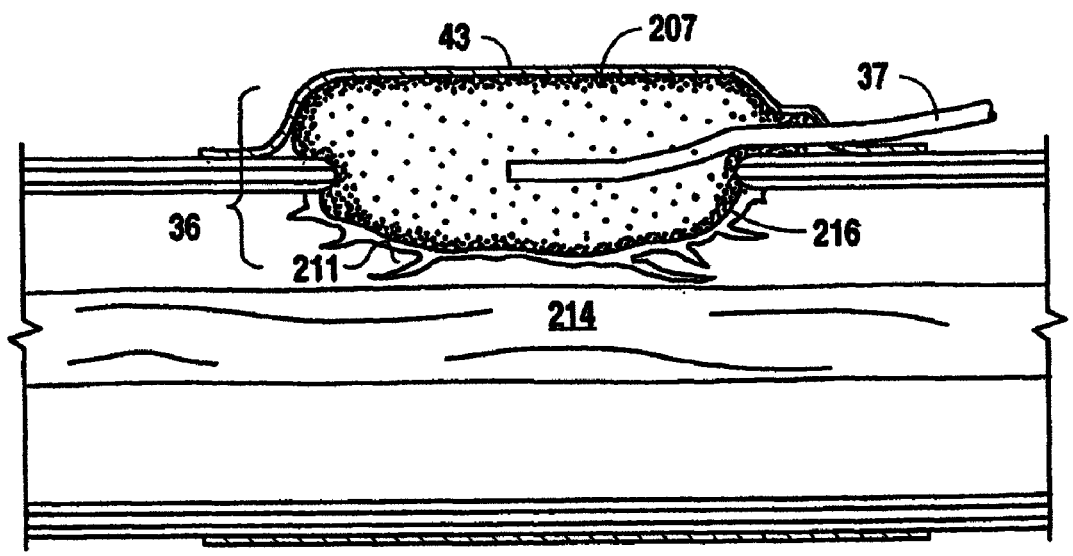
FIG. 16 is a cross section of a wound where the sprayed chemical has hardened into the contours of the wound (with tube).

Referring to FIGS. 14 through 16, another way in which the pad 36 is made is by spraying a nontoxic chemical substance 215 directly into the wound cavity 216. The chemical substance 215 hardens into the shape of the wound cavity 216 when placed directly into the wound 216. This forms a pad 36 such that the surface of the pad 36 next to the healing tissue is smooth and has pores of a diameter of approximately 100 microns or less. A chemical substance (not shown) can also be sprayed in a sterile environment before insertion into the wound cavity 216. When the pad 36 is formed on an external sterile surface it is allowed to harden slightly into a foam like substance and then pressed into the wound cavity 216 so as to conform to the wound. The chemical substances used in these circumstances are sprayed so as to make a pad 36 with a smooth outer surface containing pores with a diameter of approximately 100 microns or less.

FIG. 14A shows a cross section of chemical being sprayed into a wound. A nontoxic chemical substance 215 is sprayed from the spray nozzle 218 of a container (not shown). The chemical substance 215 is under pressure such that when it is sprayed into the wound cavity 216 of the body 214 the gas is expelled from the chemical substance 215 which allows the chemical substance 215 to expand from a liquid phase to a solid porous phase which conforms to the shape of the wound cavity 216 (See FIG. 15 where the solidification of the pad 36 is shown with a wound cover 43 placed over the pad 36 and tube 37 assembly.). The vacuum tube 37 should be placed in the cavity 216 during the spraying of the chemical substance 215 before solidification occurs (See FIG. 14B). This porous pad 36 which is formed (See FIG. 16) is equally vacuum compatible next to the vacuum tube 37 as well as compatible with the healing tissue containing a smooth surface and only micropores 207 of approximately 100 microns of less in diameter in contact with the wound cavity 216.

The type of pad 36 can vary based on the type of wound involved. In addition, the type of wound may dictate that an antimicrobial agent, such as Neosporin, be used in the pad 36 entirely or on the surface which is in contact with the wound so as to give a topical antimicrobial effect.

Figure 10:
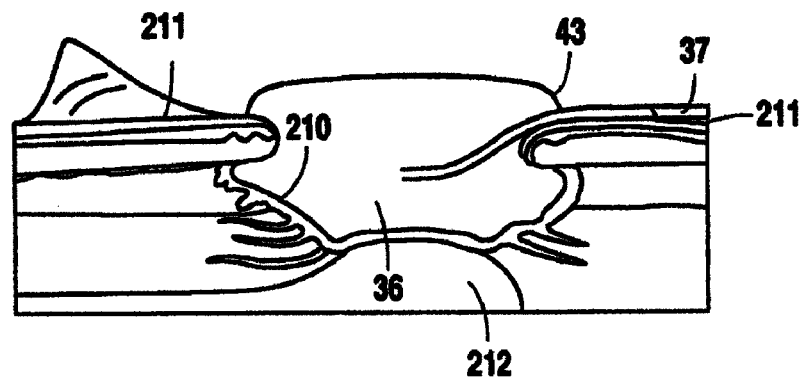
FIG. 10 is a section through a wound showing the wound pad in place.

In use, the porous pad 36 is cut to a size which corresponds closely to the edge of the wound with the objective of packing the pad 36 into the wound cavity 216 so that it contacts the surface of the cavity 216, rather than bridging the cavity 216. As depicted in FIG. 10, the cavity 216 may be extensive and there may be little or no tissue coverage to the bone 212. This is illustrated diagrammatically in FIG. 10. FIG. 10 is a cross-section through a wound showing the porous pad 36 packed in the wound cavity 216. It is important that the pad 36 should be firmly packed into the recesses of the wound cavity 216. Drainage tube 37 terminates within the center of the porous pad 36. Surgical drape 43 extends over the porous pad 36 and is adhered to intact skin around the periphery of the wound. Drape 43 is also firmly adhered around the tube 37 to prevent leakage of air. A wound cover 43 is then adhered to the surrounding skin and around the drainage tube 37 to provide an air-tight seal around the wound.

Figure 6:
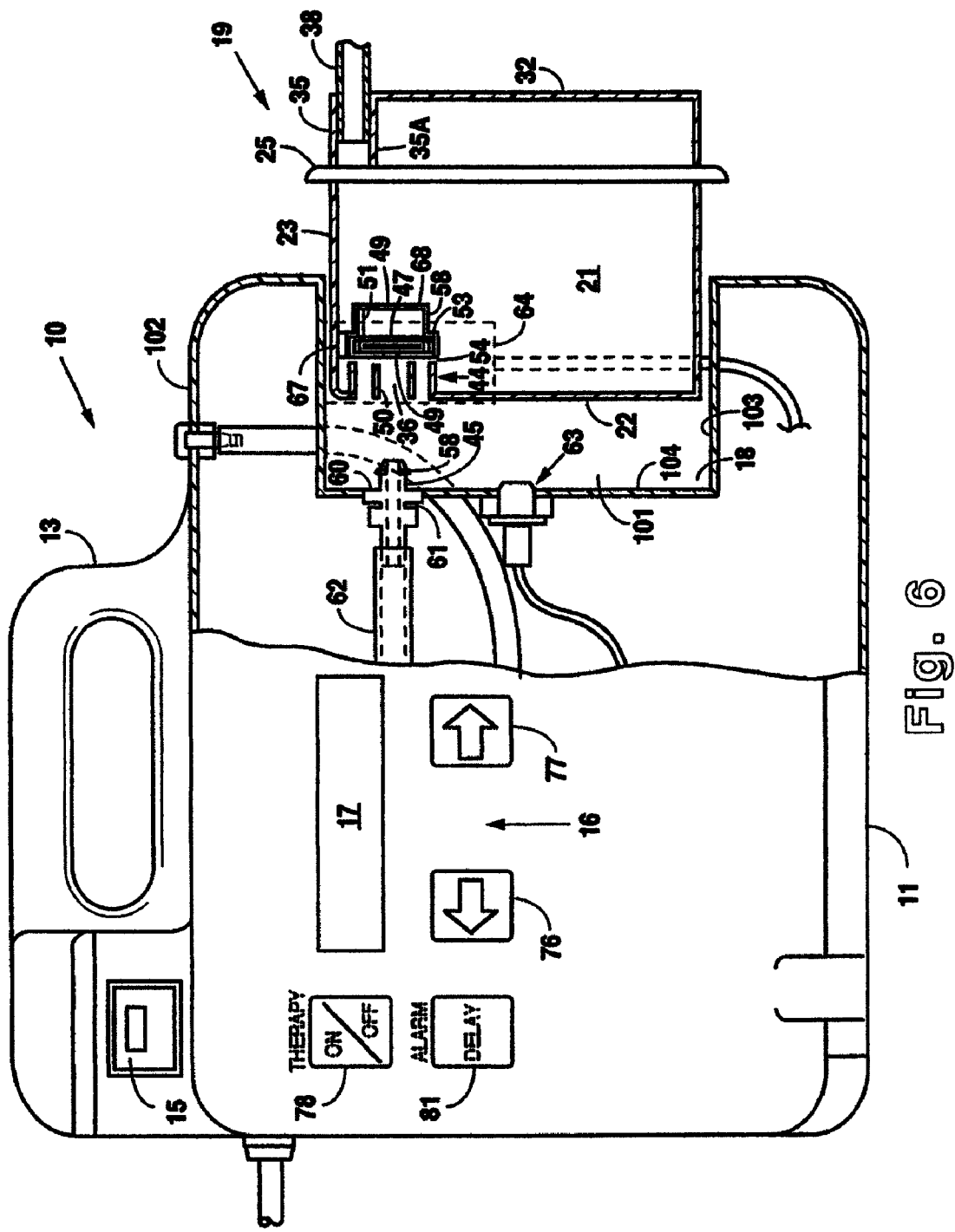
FIG. 6 is a front plan view in partial cross section depicting the connection of the wound drainage collection canister of FIG. 3 within the housing of the vacuum pump of FIG. 1.

As illustrated in FIGS. 2, 4 and 6, canister 19 includes outlet 44 that mounts over port 45 to permit wound closure apparatus 10 to draw wound fluids into canister 19. Outlet 44 is cylindrically shaped and formed as an integral part of back wall 22 by outer wall 33 and inner wall 50 which are interconnected by end wall 34. Passageway 52, defined in part by interior wall 50 and in part by filter cap 49, provides the actual conduit for outlet 44 between the interior and exterior of canister 19. The placement of canister 19 within recess 18 such that outlet 44 resides over port 45 couples canister 19 to a vacuum pump 84. The vacuum pump 84 removes air from canister 19 to create a vacuum pressure within canister 19. That vacuum pressure is then transmitted to a wound site through hoses 37 and 38, thereby not only enabling therapeutic use of system 10, but also tending to promote wound drainage. Any wound drainage fluid is then drawn through pad 36 and hoses 37 and 38 into canister 19.

Outlet 44 resides near top wall 23 of canister 19 to ensure efficient operation of the vacuum pump 84. That is, the vacuum pump 84 removes the most air from canister 19 when the air does not have to first bubble through wound fluids contained in canister 19. Consequently, with outlet 44 positioned near the top of canister 19, the vacuum pump 84 removes air directly from canister 19, and it is only during the final filling of canister 19 that air must bubble through wound fluids. Preferably, as described below, the apparatus includes detecting and warning means which operates before the level of drainage fluid reaches either the inlet or outlet tube so that a fresh canister 19 can be installed.

In removing fluids from a wound utilizing wound closure apparatus 10, a major safety concern is preventing wound fluids from contaminating the vacuum pump 84. Accordingly, filter 46 mounts over outlet 44 utilizing filter carrier 48 and filter cap 49 to block the flow of wound fluids to outlet 44 so that wound fluids remain within canister 19 and do not flow into the vacuum pump 84. In this preferred embodiment, filter 46 is a 0.2 micron hydrophobic membrane filter providing a bacterial barrier, although other filters may be substituted as appropriate.

Figure 7:
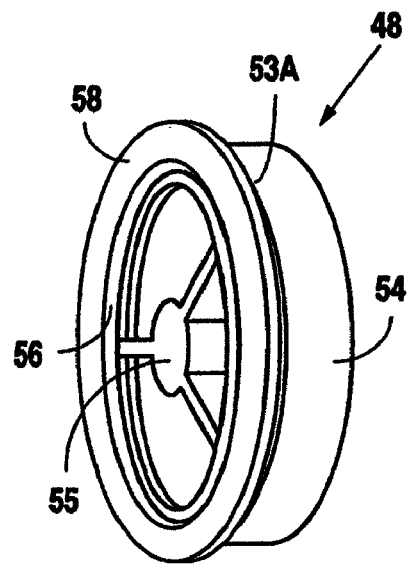
FIG. 7 is a perspective view depicting the filter carrier of the wound drainage collection canister.

As illustrated in FIG. 7, filter carrier 48 includes face 53 formed integrally with lip 54. Face 53 includes groove 56 formed therein, while lip 54 supports brace 55 in its interior. Filter 46 fits within groove 56 of face 53 and is supported within filter carrier 48 by brace 55 of lip 54. An O ring 53A is fitted in peripheral recess of filter carrier 48 to accommodate manufacturing tolerances and ensure a fluid tight seal with filter cap 49.

Figure 8:
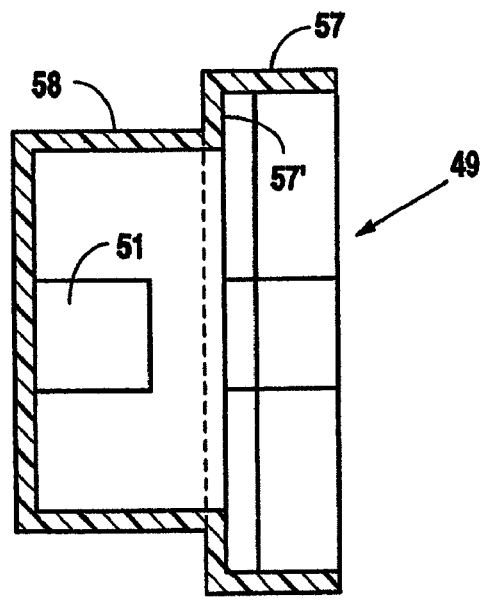
FIG. 8 is a top plan view depicting the filter cap of the wound drainage collection canister.

As illustrated in FIGS. 6 and 8, filter cap 49 includes cylindrical portions 57 and 58, which are formed integrally (with annulus 57' spanning there between), to hold filter carrier 48 within passageway 52 of outlet 44. To mount filter 46 over passageway 52, filter 46 is first placed within filter carrier 48 as described above. Filter carrier 48 is then positioned within filter cap 49 such that face 53 abuts annulus 57' of filter cap 49 and lip 54 of filter carrier 48 resides within annular lip 50' of outlet 44. Accordingly, when cylindrical portion 57 of filter cap 49 mounts over outlet 44, the front face 53 of filter carrier 48 and the outer edges of filter 46 abut annulus 57' to secure filter 46 within passageway 52. Filter cap 49 attaches to outlet 44 using any suitable means such as an adhesive or welding. Filter cap 49 is completely sealed except for aperture 51 positioned on top of filter cap 49. Aperture 51 communicates with port 45 via passageway 52 of outlet 44 to permit the vacuum pump 84 to draw air from the interior of canister 19.

As illustrated in FIGS. 2 and 6, port 45 includes O-ring 59 mounted thereabout to provide a fluid tight seal between port 45 and inner wall 50 of outlet 44. Port 45 mounts through rear wall 104 of chamber 18 using any suitable means such as nuts 60 and 61. Furthermore, line 62 attaches to the rear of port 45 using any suitable means such as a clamp to couple port 45 to the vacuum pump 84.

Switch 63 protrudes through rear wall 104 of chamber 18 to produce a signal indicating when canister 19 properly and securely resides within chamber 18. In this preferred embodiment, switch 63 is a normally open push button switch that mounts on rear wall 104 of chamber 18 using any suitable means such as a bracket. When canister 19 is properly positioned within chamber 18, its rear wall 22 presses the head of switch 63, closing switch 63 so that it provides a signal indicating that canister 19 properly resides within chamber 18.

Figure 6A:
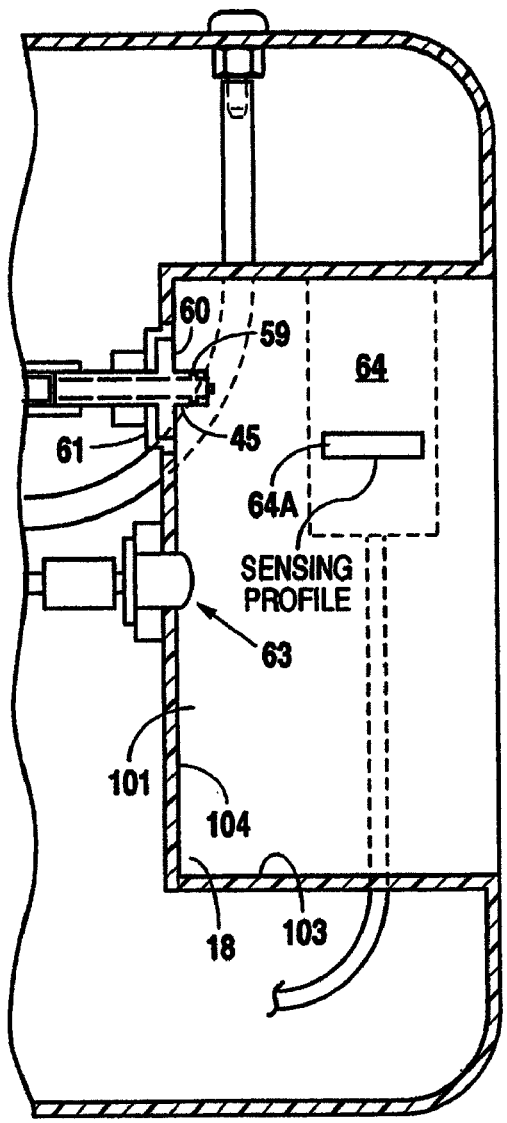
FIG. 6A is a partial view of the apparatus shown in FIG. 6 except the canister is removed.

Fill sensor 64 resides adjacent side wall 101, exterior to chamber 18. Fill sensor 64 provides a signal that indicates when canister 19 is filled with wound debris. In this preferred embodiment, fill sensor 64 is a capacitive sensor that mounts on side wall 101 of chamber 18 using any suitable means such as a bracket or appropriate adhesive material. Fill sensor 64 has a sensing profile 64A which determines the point at which the capacitance measurement is made. When wound fluids have reached the level within canister 19 which corresponds to the location of the sensing profile 64A, the capacitance within canister 19 as>seen=by fill sensor 64 changes, resulting in fill sensor 64 outputting a signal indicating that canister 19 is filled with wound fluids to the level at which the sensing profile is located. The position of this sensing profile behind wall 101 can be changed (see FIGS. 6A) to provide an optimum balance of space and volume utility.

Figure 2A:
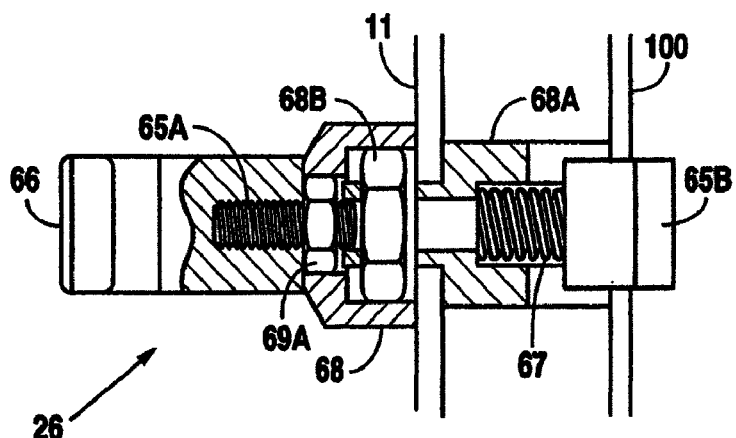
FIG. 2A is a detail view of the latch 26 portion of FIG. 2, partially cutaway to eliminate guide (or key) 29 from the view and to show portions of latch 26 in sagital cross section.

As illustrated in FIG. 2A, latch 26 generally comprises latch pin 65, handle 66, latch guide sleeve 68A and spring 67. Latch pin 65 comprises a proximal end 65A and distal end 65B. Latch guide sleeve 68A abuts the inner surface of front housing 11 and is held securely in place from the outer side of front housing 11 by nut 68B. Handle 66 screws onto the proximal end 65A of latch pin 65 and is locked in position by nut 69A. In the preferred embodiment, cover 68 over nuts 69A and 68B provides a surface against which handle 66 abuts, thus preventing end 65B from excessively entering chamber 18 as will be understood further herein. Cover 68 also provides aesthetic enclosure of nuts 69A and 68B. Dependent attachment of side wall 100 (chamber 18), as described herein above, is such that side wall 100 abuts latch guide sleeve 68A on the side distal front housing 11. Further, this arrangement causes distal end 65B of latch pin 65 to project into chamber 18 under the force of spring 67 (shown partially cut away). Spring 67 resides circumferentially about latch pin 65 within an axial bore of latch pin guide 68A. Spring 67 exerts force between distal end 65B of latch pin 65 and an annulus within the axial bore of latch pin guide 68A. A transverse slot in the distal end of latch pin guide 68A receives end 65B of latch pin 65, providing rotational alignment of end 65B and further recess for end 65B when a user pulls handle 66 in an axial direction.

Latch 26 operates to ensure canister 19 remains secured within chamber 18. End 65B of latch 26 terminates in a point that protrudes through key 29 into chamber 18. During the placing of canister 19 within chamber 18, key way 27 of canister 19 forces the point 65B of the latch pin within key 29. However, once canister 19 has been properly positioned within chamber 18, recess 28 resides below latch pin end 65B so that spring 67 biases the point 65B of latch pin 65 into recess 28 to prevent the removal of canister 19 from chamber 18. The removal of canister 19 from chamber 18 is accomplished by grasping handle 66 and pulling the point 65B of latch pin 65 from recess 28. With the point of latch pin 65 no longer within recess 28, canister 19 may be pulled from chamber 18 using its raised portion 32.

Figure 9:
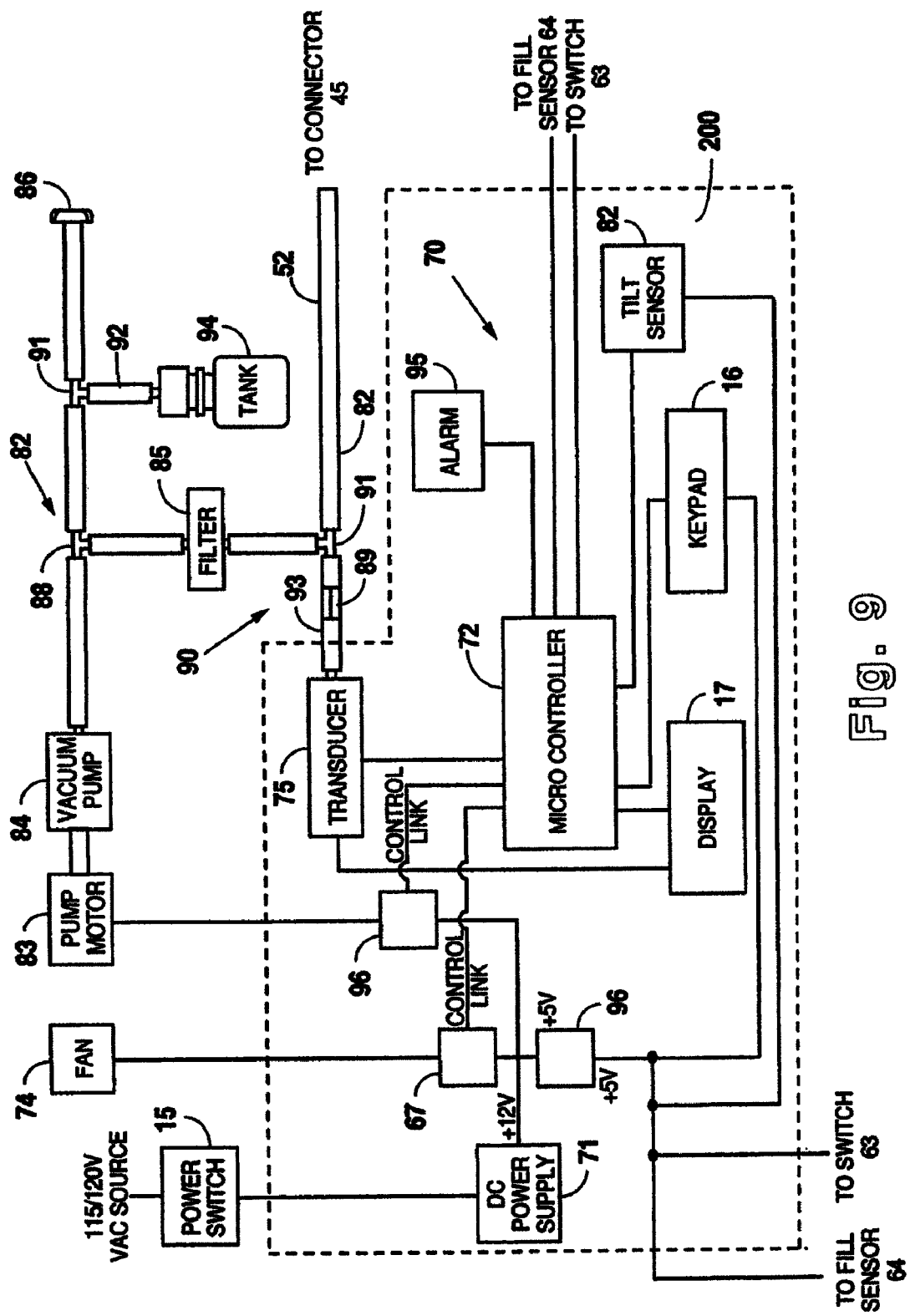
FIG. 9 is a schematic view depicting the control system for a wound closure apparatus constructed according to the teachings of the present invention.

As illustrated in FIG. 9, wound closure apparatus 10 preferably plugs into a standard 115/120 VAC power source (e.g. an outlet) to supply power to control system 70. Alternative embodiments (not shown, although similar) are readily adapted for 220 VAC power by changing the power cord and appropriately rewiring the taps of the transformer within DC power supply 71, as is readily known in the art. The application of power to control system 70 is regulated by power switch 15 which is a standard push button on/off switch. With power switch 15 depressed, DC power supply 71 receives the 115/120 VAC signal and converts it into a 12 VDC signal for use by fan 74 and vacuum pump 84. A conventional voltage regulator 96 steps down the voltage to +5V for use by each of the other DC components 16, 17, 63, 64, 72, and 75. Voltage regulator 96 connects to keypad 16, LCD 17, switch 63, fill sensor 64, microcontroller 72, transducer 75, and tilt sensor 82 to supply each of them with the +5V DC signal. Microcontroller 72 links to solid state relays (MOSFETs) 97 and 98 for controlling the provision of the 12 VDC power supply to fan 74 and pump motor 83, respectively.

As illustrated in FIG. 1, once power switch 15 is depressed, a user employs keypad 16 and LCD 17 to select the operating parameters for wound closure apparatus 10. Wound closure apparatus 10 stores the previously selected operating parameters so that upon power initialization, LCD 17 displays the phrase NEW PATIENT with the word NO over arrow button 76, and the word YES over arrow button 77. If the user presses arrow button 76 to answer no, wound closure apparatus 10 will operate at the previously selected parameters. After answer no, the user pressures on/off button 78 to begin operation of wound closure apparatus 10.

Conversely, if the user presses arrow button 77 to indicate a new patient, wound closure apparatus 10 will operate either under default values or allow the user to select the operating parameters. To operate under default parameters, the user presses on/off button 78 after pressing arrow button 77. However, to select his or her own values, the user presses option button 79 after pressing arrow button 77.

Upon the pressing of options button 79, LCD 17 displays a bar graph representing the spectrum of available vacuum pump pressures and a numerical representation of the vacuum pump pressure presently displayed by the bar graph. The user changes vacuum pump pressure using arrow buttons 76 and 77. The pressing of arrow button 76 reduces vacuum pump pressure, while the pressing of arrow button 77 increases vacuum pump pressure. After selecting the desired vacuum pump pressure, the user presses option button 79 to save the selected vacuum pump pressure.

Once the selected vacuum pump pressure has been saved, LCD 17 displays the pump operation times available to the user. The user may program wound closure apparatus 10 to pump either continuously or intermittently. Thus, LCD 17 displays the word CONTINUOUS over arrow button 76b and INTERMITTENT over arrow button 77. The user selects continuous operation by pressing arrow button 76 followed by on/off button 78 to activate the vacuum pump 84. In its continuous mode, wound closure apparatus 10 runs its vacuum pump 84 continuously until on/off button 78 is pressed again.

If the user presses arrow button 77 to select intermittent operation, LCD 17 displays a bar graph representing the minimum and maximum on times for the vacuum pump 84. LCD 17 also displays the phase ON TIME and the numerical value presently displayed by the bar graph. A user decreases the on time of the vacuum pump 84 by pressing arrow button 76 and increases the on time of the vacuum pump 84 by pressing arrow button 77. After selecting the desired on time, the user presses options button 79 to save the selected on time value.

LCD 17 then displays a second bar graph representing the off time for the vacuum pump 84 with the phrase OFF TIME and the numerical value presently depicted by the bar graph. Again, arrow buttons 76 and 77 are pressed to increase or decrease, respectively, the off time for the vacuum pump 84. After selecting the off time, the user presses options button 79 followed by on/off button 78 to operate wound closure apparatus 10 using the selected parameters.

Keypad 16 includes setting button 80 to permit the user to sequentially display the currently selected operating parameters of wound closure apparatus 10. Keypad 16 further includes delay button 81 to permit the user to deactivate an alarm sounded in response to an improper operating condition of wound closure apparatus 10. Delay button 81 provides the user with the ability to silence alarms so that the alarm will not have to be listened to during the correction of the problem.

Any new alarm conditions occurring within the fifteen minute period (delay period) after the pressing of delay button 81 will not be indicated by an audible alarm. However, the pump will still be deactivated when appropriate, even during the delay period.

Again referring to FIG. 9, microcontroller 72 is a multi-port microprocessor with a ten-bit analog to digital (A/D) converter having associated memory that stores the program directing microcontroller 72 during its controls of wound closure apparatus 10. After receiving and storing the user selected operational parameters and receiving an on signal due to the pressing of on/off button 78, microcontroller 72 activates pump motor 83 which, in turn, drives vacuum pump 84 to begin the removal of air from canister 19.

As vacuum pump 84 operates, it draws air from within canister 19, into line 62 via outlet 44 of canister 19 and port 45. Line 62 connects to filter 85 and transducer 75 via T-junction 91. Filter 85 is similar to filter 46 and thus ensures no wound fluids contaminate vacuum pump 84. Filter 85 communicates with pump 84 via T-junction 88 and one arm of the latter is connected to bleed valve 86. Bleed valve 86 communicates with the atmosphere to release pressure developed within line 62 by vacuum pump 84 after microcontroller 72 deactivates vacuum pump 84. Bleed valve 86 is sufficiently small to ensure that it generally does not affect the vacuum pressure levels achieved by vacuum pump 84 as it evacuates air from canister 19, except to prevent over pressurization beyond 250 mm Hg and to prevent erratic operation of the vacuum pump 84 at very low pressure settings.

In the preferred embodiment, an orifice of 0.5 mm diameter is especially preferred for bleed valve 86. Valve 86 or the equivalent is particularly important for enabling intermittent application of negative pressure, as the orifice 86 allows for gradual release of the negative pressure (over a period of about fifteen seconds) when the pump motor 83 is de-actuated. Bleed valve 86 is positioned outside housing 11 to facilitate un-clogging of aperture 86 in the event of a blockage. An aperture is provided in bleed valve 86, which is machined from stainless steel. Flow control orifices would be alternatives.

Line 62 also includes T-connector 91 to connect it with line 92. Line 92 is connected to tank 94 which acts as a damper to pressure changes in line 62. This dampening effect, facilitated by restrictor 89 in line 93 between transducer 75 and T-junction 91, causes the pressure measured by transducer 75 to be an accurate indication of actual wound site pressure. Transducer 75 communicates with line 62 via line 93 to measure tank 94 pressure and produce an electrical signal representative of that pressure. Transducer 75 outputs its pressure signal to microcontroller 72.

Microcontroller 72 utilizes the pressure signal to control the speed of pump motor 83. As previously described, the user selects either a default vacuum pump pressure or a desired vacuum pump pressure for the operation of wound closure apparatus 10. After receiving the wound pressure signal from transducer 75, microcontroller 72 compares the wound pressure with the user selected pressure. If the wound pressure is higher than the user selected vacuum pump pressure, microcontroller 72 reduces pump motor speed to decrease vacuum pump pressure and thus the pressure at the wound. Conversely, if the wound pressure is less than the user selected vacuum pump pressure, microcontroller 72 increases the speed of pump motor 83 resulting in an increase in the vacuum pressure applied at the wound.

Microcontroller 72 controls pump motor 83 by varying the amount of voltage received by pump motor 83. That is, microcontroller 72 receives the 12 VDC signal from DC power supply 71 and outputs a voltage between 0 and 12 VDC to pump motor 83 to control its speed in accordance with the user selected vacuum pump pressure value. Accordingly, microcontroller 72 employs feedback to ensure that the wound experiences the user selected vacuum pump pressure. If the target pressure is not reached after a period of five minutes, microcontroller 72 deactivates motor 83 and sounds the audible alarm. Additionally, the feedback signal prevents maximum vacuum pump pressure from being exceeded. If the wound pressure measured by transducer 75 exceeds a maximum safe vacuum pump pressure microcontroller 72 deactivates pump motor 83 and activates alarm 95 to signal a malfunction.

Wound closure apparatus 10 includes fan 74 to cool pump motor 83 and printed circuit (PC) board 200 during the operation of the wound closure apparatus 10. In the preferred embodiment, microcontroller 72 controls fan 74 to always operate while power is being supplied. In alternative embodiments, however, microcontroller 72 controls fan 74 to operate only in relation to motor 83, because it is only necessary for fan 74 to operate if motor 83 is also operating. In such alternative, as long as pump motor 83 operates, microcontroller 72 runs fan 74. However, when microcontroller 72 deactivates pump motor 83 it also deactivates fan 74.

Control system 70 includes fill sensor 64 to provide a signal to microcontroller 72 that indicates when canister 19 is completely filled with wound fluids. After receiving a signal from fill sensor 64, microcontroller 72 deactivates pump motor 83 and fan 74 and activates alarm 95 to signal the user that canister 19 must be replaced.

Control system 70 includes switch 63 to prevent users from operating wound closure apparatus 10 without a canister properly installed. If a canister is not properly installed, switch 63 remains open and therefore outputs no signal to microcontroller 72. If microcontroller 72 receives no signal from switch 63, indicating no canister within chamber 18, it will not supply power to pump motor 83 even after a user has pressed on/off button 78. Furthermore, microcontroller 72 activates alarm 95 to signal the user that either a canister is not properly installed or is improperly installed within chamber 81. Microcontroller 72 operates pump motor 83 only if switch 63 is depressed to provide a signal indicating the proper placement of a canister within chamber 18.

Control system 70 includes tilt sensor 82 to prevent operation of wound closure apparatus 10 if it is tilted excessively. Excessive tilting of wound closure apparatus 10 during operating diminishes the efficiency of removal of wound fluids and, more importantly, might result in either the contamination of vacuum pump 84 or the spilling of wound fluids. Thus, if wound closure apparatus 10 tilts along any of its axes beyond a predetermined angle (approximately 45N in this preferred embodiment), tilt sensor 82 outputs a signal to microcontroller 72. In response, microcontroller 72 deactivates pump motor 83 and activates alarm 95 to signal the user of the excessive tilt situation. In this preferred embodiment, tilt sensor 82 may be implemented with any standard mercury switch. A predetermined delay (e.g. 30 seconds) may be incorporated in the circuitry so that the tilt alarm does not operate immediately.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A porous pad for providing a reduced pressure to a tissue site comprising:
   a porous material formed by spraying a chemical substance that cures to form the porous material having a body and an outer surface, both the body and the outer surface having pores wherein the average size of the pores in the outer surface is smaller than the average size of the pores in the body, and a portion of the outer surface substantially conformable to the shape of the tissue site; and
   a pathway formed within the porous material and adapted to fluidly communicate with a source of reduced pressure.

2. The pad of claim 1, wherein the average size of the pores in the outer surface is about 100 microns or less in diameter.

3. The pad of claim 1, wherein the chemical substance cures and hardens to form the porous material after spraying the chemical substance.

4. The pad of claim 1, wherein the sprayed chemical substance expands to form the porous material after the chemical substance is sprayed.

5. The pad of claim 1, wherein the porous material includes an antimicrobial agent.

6. The pad of claim 1, wherein the chemical substance comprises a pressurized liquid before being sprayed and expels gas from the pressurized liquid when sprayed, whereby the chemical substance expands and hardens to form the porous material.

7. The pad of claim 1, wherein the porous material is formed by spraying the chemical substance directly onto the tissue site.

8. The pad of claim 1, wherein the porous material is formed by spraying the chemical substance onto a surface other than the tissue site.

9. A tissue treatment system comprising:
   a porous material formed by spraying a chemical substance that cures to form the porous material having a body and an outer surface, both the body and the outer surface having pores wherein the average size of the pores in the outer surface is smaller than the average size of the pores in the body, and a portion of the outer surface substantially conformable to the shape of the tissue site;
   a pathway formed within the porous material and adapted to fluidly communicate with a source of reduced pressure whereby reduced pressure is provided to the tissue site; and
   a conduit operable to deliver the reduced pressure, a first end of the conduit being connectable to the pathway and a second end of the conduit being connectable to the source of reduced pressure.

10. The system of claim 9, wherein the first end of the conduit extends into the porous material.

11. The system of claim 9, further comprising a drape adapted to cover the porous material.

\* \* \* \* \*